(12) United States Patent
Wasdyke et al.

(10) Patent No.: US 10,405,878 B2
(45) Date of Patent: Sep. 10, 2019

(54) ROTATABLE MEDICAL DEVICE

(71) Applicant: BOSTON SCIENTIFIC SCIMED, INC., Maple Grove, MN (US)

(72) Inventors: Joel M. Wasdyke, Eden Prairie, MN (US); Sanjeev Kulkarni, Plymouth, MN (US); Tate Augustin, Eden Prairie, MN (US); Joel R. Brey, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 600 days.

(21) Appl. No.: 14/805,354

(22) Filed: Jul. 21, 2015

(65) Prior Publication Data

US 2016/0022307 A1    Jan. 28, 2016

Related U.S. Application Data

(60) Provisional application No. 62/029,281, filed on Jul. 25, 2014.

(51) Int. Cl.
*A61B 17/3207* (2006.01)
*A61B 17/22* (2006.01)
*A61B 17/32* (2006.01)
*A61B 90/00* (2016.01)

(52) U.S. Cl.
CPC ............... *A61B 17/320758* (2013.01); *A61B 2017/22077* (2013.01); *A61B 2017/22094* (2013.01); *A61B 2017/320004* (2013.01); *A61B 2090/034* (2016.02)

(58) Field of Classification Search
CPC .. A61B 17/320758; A61B 2017/22077; A61B 2017/22094; A61B 2017/320004; A61B 2090/034
USPC .................................. 606/159, 168, 170, 180
See application file for complete search history.

(56) References Cited

U.S. PATENT DOCUMENTS

| 4,445,509 A | 5/1984 | Auth |
| 4,684,361 A | 8/1987 | Feldman et al. |
| 4,692,136 A | 9/1987 | Feldman et al. |
| 4,718,888 A | 1/1988 | Darnell |
| 4,898,575 A | 2/1990 | Fischell et al. |
| 4,990,134 A | 2/1991 | Auth |
| 5,263,959 A | 11/1993 | Fischell |
| 5,312,427 A | 5/1994 | Shturman |
| 5,314,407 A | 5/1994 | Auth et al. |
| 5,314,438 A | 5/1994 | Shturman |
| 5,356,418 A | 10/1994 | Shturman |
| 5,360,432 A | 11/1994 | Shturman |

(Continued)

FOREIGN PATENT DOCUMENTS

WO    2006011970 A1    2/2006

*Primary Examiner* — Vy Q Bui
(74) *Attorney, Agent, or Firm* — Seager, Tufte & Wickhem LLP

(57) ABSTRACT

A rotational atherectomy device including a drive shaft rotatably extending through an outer tubular member to rotate a cutting member positioned at a distal end thereof. The rotational atherectomy device further includes an elongate penetrator extendable distal of the cutting member a predetermined maximum distance and configured to stabilize the cutting member as the cutting member engages an occlusion to control the trajectory and advancement of the cutting member through the occlusion.

20 Claims, 8 Drawing Sheets

(56) References Cited

U.S. PATENT DOCUMENTS

| | | | |
|---|---|---|---|
| 5,423,846 A | 6/1995 | Fischell | |
| 5,443,443 A * | 8/1995 | Shiber | A61B 17/22012 |
| | | | 604/22 |
| 5,554,163 A | 9/1996 | Shturman | |
| 5,628,761 A | 5/1997 | Rizik | |
| 5,667,490 A | 9/1997 | Keith et al. | |
| 5,672,945 A | 9/1997 | Krause | |
| 5,681,336 A * | 10/1997 | Clement | A61B 17/32075 |
| | | | 604/96.01 |
| 5,746,758 A | 5/1998 | Nordgren et al. | |
| 5,766,190 A | 6/1998 | Wulfman | |
| 5,779,721 A | 7/1998 | Nash | |
| 5,779,722 A | 7/1998 | Shturman et al. | |
| 5,893,857 A | 4/1999 | Shturman et al. | |
| 5,897,566 A | 4/1999 | Shturman et al. | |
| 5,897,567 A | 4/1999 | Ressemann et al. | |
| 5,928,218 A | 7/1999 | Gelbfish | |
| 6,001,112 A | 12/1999 | Taylor | |
| 6,024,749 A | 2/2000 | Shturman et al. | |
| 6,027,460 A | 2/2000 | Shturman | |
| 6,039,747 A | 3/2000 | Shturman et al. | |
| 6,077,282 A | 6/2000 | Shturman et al. | |
| 6,080,170 A | 6/2000 | Nash et al. | |
| 6,090,122 A | 7/2000 | Sjostrom et al. | |
| 6,129,734 A | 10/2000 | Shturman et al. | |
| 6,132,444 A | 10/2000 | Shturman et al. | |
| 6,206,898 B1 | 3/2001 | Honeycutt et al. | |
| 6,217,595 B1 | 4/2001 | Shturman et al. | |
| 6,295,712 B1 | 10/2001 | Shturman et al. | |
| 6,454,779 B1 | 9/2002 | Taylor | |
| 6,494,890 B1 | 12/2002 | Shturman et al. | |
| 6,500,186 B2 | 12/2002 | Lafontaine et al. | |
| 6,565,588 B1 | 5/2003 | Clement et al. | |
| 6,638,288 B1 | 10/2003 | Shturman et al. | |
| 6,818,001 B2 | 11/2004 | Wulfman et al. | |
| 6,852,118 B2 | 2/2005 | Shturman et al. | |
| 6,981,941 B2 | 1/2006 | Whiteman et al. | |
| 7,174,240 B2 | 2/2007 | Shturman et al. | |
| 7,175,605 B2 | 2/2007 | Tiedtke et al. | |
| 7,344,546 B2 | 3/2008 | Wulfman et al. | |
| 7,479,147 B2 | 1/2009 | Honeycutt et al. | |
| 7,485,127 B2 | 2/2009 | Nistal | |
| 7,507,245 B2 | 3/2009 | Shturman et al. | |
| 7,534,249 B2 | 5/2009 | Nash et al. | |
| D600,792 S | 9/2009 | Eubanks et al. | |
| 7,584,022 B2 | 9/2009 | Shturman et al. | |
| D607,102 S | 12/2009 | Robinson | |
| D610,258 S | 2/2010 | Robinson | |
| 7,666,202 B2 | 2/2010 | Prudnikov et al. | |
| 7,674,272 B2 | 3/2010 | Torrance et al. | |
| 7,713,231 B2 | 5/2010 | Wulfman et al. | |
| 7,713,235 B2 | 5/2010 | Torrance et al. | |
| 7,842,009 B2 | 11/2010 | Torrance et al. | |
| 8,109,954 B2 | 2/2012 | Shturman | |
| 8,109,955 B2 | 2/2012 | Shturman | |
| 8,137,369 B2 | 3/2012 | Shturman | |
| 8,142,458 B2 | 3/2012 | Shturman | |
| 8,147,507 B2 | 4/2012 | Shturman | |
| 8,157,825 B2 | 4/2012 | Shturman | |
| 8,162,964 B2 | 4/2012 | Piippo et al. | |
| 8,177,801 B2 | 5/2012 | Kallok et al. | |
| 8,192,451 B2 | 6/2012 | Cambronne et al. | |
| 8,241,315 B2 * | 8/2012 | Jenson | A61B 17/3207 |
| | | | 606/194 |
| 8,348,965 B2 | 1/2013 | Prudnikov et al. | |
| 8,353,923 B2 | 1/2013 | Shturman | |
| 8,388,636 B2 | 3/2013 | Shturman | |
| 8,388,637 B2 | 3/2013 | Shturman | |
| 8,439,937 B2 | 5/2013 | Montague et al. | |
| 8,454,638 B2 | 6/2013 | Shturman | |
| 8,465,510 B2 | 6/2013 | Shturman | |
| 8,475,478 B2 | 7/2013 | Robinson | |
| 8,496,678 B2 | 7/2013 | Shturman | |
| 8,500,764 B2 | 8/2013 | Shturman | |
| 8,500,765 B2 | 8/2013 | Shturman | |
| 8,551,128 B2 | 10/2013 | Hanson et al. | |
| 8,568,418 B2 | 10/2013 | Matusaitis et al. | |
| 8,597,313 B2 | 12/2013 | Thatcher et al. | |
| 2002/0082637 A1 | 6/2002 | Lumauig | |
| 2003/0078594 A1 | 4/2003 | Shturman et al. | |
| 2003/0120296 A1 | 6/2003 | Shturman et al. | |
| 2003/0125756 A1 | 7/2003 | Shturman et al. | |
| 2004/0006358 A1 | 1/2004 | Wulfman et al. | |
| 2004/0181249 A1 | 9/2004 | Torrance et al. | |
| 2004/0220519 A1 | 11/2004 | Wulfman et al. | |
| 2004/0230212 A1 | 11/2004 | Wulfman | |
| 2004/0230213 A1 | 11/2004 | Wulfman et al. | |
| 2004/0235611 A1 | 11/2004 | Nistal | |
| 2004/0236312 A1 | 11/2004 | Nistal et al. | |
| 2004/0243162 A1 | 12/2004 | Wulfman et al. | |
| 2006/0235453 A1 | 10/2006 | Shturman et al. | |
| 2006/0249205 A1 | 11/2006 | Shturman et al. | |
| 2006/0258976 A1 | 11/2006 | Shturman et al. | |
| 2006/0271242 A1 | 11/2006 | Shturman et al. | |
| 2008/0103439 A1 | 5/2008 | Torrance et al. | |
| 2008/0103446 A1 | 5/2008 | Torrance et al. | |
| 2008/0103516 A1 | 5/2008 | Wulfman et al. | |
| 2008/0228208 A1 | 9/2008 | Wulfman et al. | |
| 2008/0306498 A1 | 12/2008 | Thatcher et al. | |
| 2008/0319462 A1 | 12/2008 | Montague et al. | |
| 2009/0012548 A1 | 1/2009 | Thatcher et al. | |
| 2009/0018564 A1 | 1/2009 | Shturman | |
| 2009/0069829 A1 | 3/2009 | Shturman | |
| 2009/0105736 A1 | 4/2009 | Prudnikov et al. | |
| 2009/0132777 A1 | 5/2009 | Kelly et al. | |
| 2009/0149877 A1 | 6/2009 | Hanson et al. | |
| 2009/0182359 A1 | 7/2009 | Shturman | |
| 2009/0264908 A1 | 10/2009 | Kallok et al. | |
| 2009/0299391 A1 | 12/2009 | Rivers et al. | |
| 2009/0299392 A1 | 12/2009 | Rivers | |
| 2009/0306657 A1 | 12/2009 | Piippo et al. | |
| 2009/0306689 A1 | 12/2009 | Welty et al. | |
| 2009/0306690 A1 | 12/2009 | Rivers et al. | |
| 2009/0306691 A1 | 12/2009 | Cambronne et al. | |
| 2009/0318942 A1 | 12/2009 | Shturman | |
| 2009/0326568 A1 | 12/2009 | Shturman | |
| 2010/0010522 A1 | 1/2010 | Shturman | |
| 2010/0049226 A1 | 1/2010 | Shturman | |
| 2010/0036402 A1 | 2/2010 | Hanson et al. | |
| 2010/0100110 A1 | 4/2010 | Cambronne et al. | |
| 2010/0121361 A1 | 5/2010 | Plowe et al. | |
| 2010/0198239 A1 | 8/2010 | McBroom et al. | |
| 2010/0211088 A1 | 8/2010 | Narveson | |
| 2010/0292720 A1 | 11/2010 | Thatcher et al. | |
| 2010/0324472 A1 | 12/2010 | Wulfman | |
| 2011/0009888 A1 | 1/2011 | Shturman | |
| 2011/0040238 A1 | 2/2011 | Wulfman et al. | |
| 2011/0071440 A1 | 3/2011 | Torrance et al. | |
| 2011/0077673 A1 | 3/2011 | Grubac et al. | |
| 2011/0087254 A1 | 4/2011 | Welty | |
| 2011/0106004 A1 | 5/2011 | Eubanks et al. | |
| 2011/0112562 A1 | 5/2011 | Torrance | |
| 2011/0118660 A1 | 5/2011 | Torrance et al. | |
| 2011/0144671 A1 | 6/2011 | Piippo Svendsen et al. | |
| 2011/0151463 A1 | 6/2011 | Wulfman | |
| 2011/0202079 A1 | 8/2011 | Schoenle et al. | |
| 2011/0208221 A1 | 8/2011 | Gennrich et al. | |
| 2011/0213391 A1 | 9/2011 | Rivers et al. | |
| 2011/0300010 A1 | 12/2011 | Jarnagin et al. | |
| 2012/0035588 A1 | 2/2012 | Schoenle et al. | |
| 2012/0035633 A1 | 2/2012 | Shturman | |
| 2012/0041359 A1 | 2/2012 | Schoenle et al. | |
| 2012/0046599 A1 | 2/2012 | Schoenle et al. | |
| 2012/0046600 A1 | 2/2012 | Kohler et al. | |
| 2012/0109105 A1 | 5/2012 | Cambronne | |
| 2012/0109170 A1 | 5/2012 | Shturman | |
| 2012/0116431 A1 | 5/2012 | Shturman | |
| 2012/0150207 A1 | 6/2012 | Shturman | |
| 2012/0165846 A1 | 6/2012 | Shturman | |
| 2012/0165847 A1 | 6/2012 | Shturman | |
| 2012/0172903 A1 | 7/2012 | Shturman | |
| 2012/0179179 A1 | 7/2012 | Shturman | |
| 2012/0191113 A1 | 7/2012 | Shturman | |
| 2013/0018398 A1 | 1/2013 | Rivers et al. | |

(56) References Cited

U.S. PATENT DOCUMENTS

| | | |
|---|---|---|
| 2013/0178881 A1 | 7/2013 | Shturman |
| 2013/0204280 A1 | 8/2013 | Shturman |
| 2013/0245654 A1 | 9/2013 | Shturman |
| 2013/0253552 A1 | 9/2013 | Schoenle et al. |
| 2013/0274773 A1 | 10/2013 | Shturman et al. |
| 2013/0296904 A1 | 11/2013 | Shturman |
| 2013/0296905 A1 | 11/2013 | Shturman |
| 2013/0310859 A1 | 11/2013 | Shturman |

* cited by examiner

ROTATABLE MEDICAL DEVICE

CROSS-REFERENCE TO RELATED APPLICATIONS

This application claims priority to U.S. Provisional Application Ser. No. 62/029,281, filed Jul. 25, 2014, the entirety of which is incorporated herein by reference.

TECHNICAL FIELD

The disclosure is directed to devices and methods for removing occlusive material from a body lumen. More particularly, the disclosure is directed to a rotational atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a rotatable cutting element thereon is advanced through the occlusion to form or enlarge a pathway through the occlusion. Typically, a guidewire is initially placed across the occlusion and then the atherectomy catheter is advanced over the guidewire as the atherectomy catheter is passed through the occlusion. However, in some instances in which there is an insufficient lumen through which to pass the guidewire, such as a chronic total occlusion (CTO), it may be difficult or impossible to position a guidewire across the occlusion for the atherectomy catheter to follow when the cutting element engages the occlusion.

Therefore, a need remains for alternative ways to penetrate and traverse occlusions, such as chronic total occlusions, to form or enlarge a pathway through the occlusion to improve blood flow through the blood vessel.

BRIEF SUMMARY

The disclosure is directed to several alternative designs, materials and methods of manufacturing medical device structures and assemblies, and uses thereof.

Accordingly, one illustrative example is a rotational atherectomy device. The rotational atherectomy device includes an outer tubular member having a lumen extending therethrough, a cutting member rotationally positioned at a distal end of the outer tubular member, and a drive shaft extending through the lumen of the outer tubular member. The drive shaft is rotatable relative to the outer tubular member to rotate the cutting member. The rotational atherectomy device further includes an elongate penetrator extendable distal of the cutting member a maximum distance, wherein the maximum distance is predetermined.

Additionally or alternatively, the elongate penetrator is a guidewire positionable through a lumen, such as a guidewire lumen, extending through the drive shaft and the cutting member.

Additionally or alternatively, the elongate penetrator includes an engagement feature configured to engage an engagement feature of the lumen when extended to the maximum distance.

Additionally or alternatively, the elongate penetrator includes a proximal portion having a first diameter and a distal portion having a second diameter less than the first diameter of the proximal portion of the elongate penetrator, and the lumen includes a proximal portion having a first diameter and a distal portion having a second diameter less than the first diameter of the proximal portion of the lumen. The second diameter of the elongate penetrator is less than the second diameter of the lumen and the first diameter of the elongate penetrator is greater than the second diameter of the lumen, such that only the distal portion of the elongate penetrator is positionable through the distal portion of the lumen.

Additionally or alternatively, the engagement feature of the elongate penetrator includes a transition in diameter and the engagement feature of the lumen includes a transition in diameter.

Additionally or alternatively, the transition in diameter of the lumen is located proximate the cutting member.

Additionally or alternatively, the elongate penetrator is rotatable with the cutting member.

Additionally or alternatively, a proximal end of the elongate penetrator is fixedly secured to the cutting member.

Additionally or alternatively, the cutting member is rotatable independent of the elongate penetrator.

Additionally or alternatively, a proximal end of the elongate penetrator is rotatably coupled to the cutting member.

Additionally or alternatively, the elongate penetrator includes a sharpened distal tip.

Additionally or alternatively, the maximum distance is in the range of 0.5 millimeters to 2.0 millimeters, particularly in the range of 0.8 millimeters to 1.2 millimeters, more particularly about 1.0 millimeter.

An illustrative example that may optionally be used in conjunction with any of the above described characteristics is a rotational atherectomy device. The rotational atherectomy device includes an outer tubular member having a lumen extending therethrough, a cutting member rotationally positioned at a distal end of the outer tubular member, and a drive shaft extending through the lumen of the outer tubular member. The drive shaft is rotatable relative to the outer tubular member to rotate the cutting member. The rotational atherectomy device further includes a guidewire lumen extending through the drive shaft and the cutting member, and an elongate guidewire extendable through the guidewire lumen. The guidewire includes distal tip and a stop configured to engage a stop in the guidewire lumen to prevent distal advancement of the distal tip of the guidewire beyond a predetermined distance distally beyond the cutting member.

Additionally or alternatively, the stop of the guidewire includes a transition in diameter and the stop of the guidewire lumen includes a transition in diameter.

Additionally or alternatively, the transition in diameter of the guidewire is located between a proximal portion of the guidewire having a first diameter and a distal portion of the guidewire having a second diameter less than the first diameter of the proximal portion of the guidewire, and the transition in diameter of the guidewire lumen is located between a proximal portion of the guidewire lumen having a first diameter and a distal portion of the guidewire lumen having a second diameter less than the first diameter of the proximal portion of the guidewire lumen. The second diameter of the guidewire is less than the second diameter of the guidewire lumen and the first diameter of the guidewire is greater than the second diameter of the guidewire lumen, such that only the distal portion of the guidewire is positionable through the distal portion of the guidewire lumen.

Additionally or alternatively, the transition in diameter of the guidewire lumen is located proximate the cutting member.

Additionally or alternatively, the predetermined distance is in the range of 0.5 millimeters to 2.0 millimeters.

Another illustrative example is method of creating or enlarging a passageway through an occlusion in a body lumen. The method includes advancing a rotational atherectomy device through a body lumen to a location proximal of an occlusion in the body lumen. The rotational atherectomy device includes a rotatable drive shaft extending through an outer tubular member to rotatably drive a cutting member positioned at a distal end of the outer tubular member, and an elongate penetrator extending distally from the cutting member. The method further includes penetrating the occlusion with the elongate penetrator, and, thereafter, rotating the cutting member with the drive shaft while advancing the cutting member through the occlusion.

Additionally or alternatively, the step of advancing the rotational atherectomy device to the location proximal of the occlusion is performed without previously positioning a guidewire across the occlusion.

Additionally or alternatively, the elongate penetrator is axially movable distally through the cutting member such that distal advancement of a distal tip of the penetrator is prevented beyond a predetermined distance distally beyond the cutting member.

Another illustrative example is a method of assembling a rotational atherectomy device. The method includes extending a guidewire distally through a guidewire lumen of a rotational atherectomy device. The rotational atherectomy device includes a rotatable drive shaft extending through an outer tubular member to rotatably drive a cutting member positioned at a distal end of the outer tubular member. The guidewire lumen extends through the rotatable drive shaft and the cutting member. The method further includes preventing distal advancement of a distal tip of the guidewire beyond a predetermined maximum distance from the cutting member.

Additionally or alternatively, the guidewire includes an engagement feature configured to engage an engagement feature of the guidewire lumen when the guidewire is extended to the predetermined maximum distance.

Additionally or alternatively, the predetermined maximum distance is in the range of 0.5 millimeters to 2.0 millimeters, preferably about 1.0 millimeter.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
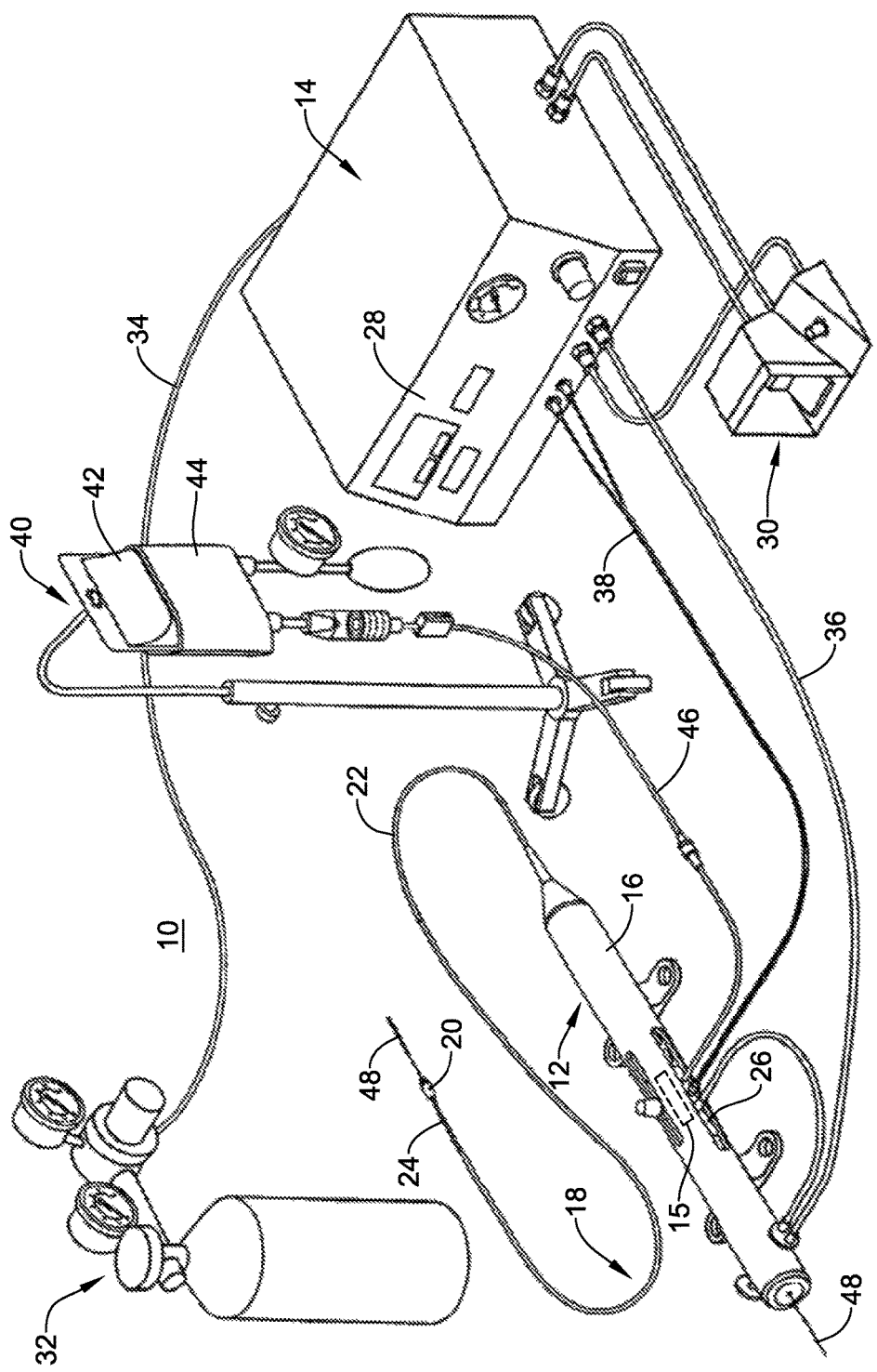
FIG. 1 illustrates an exemplary atherectomy system.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary rotational atherectomy system 10 is shown in FIG. 1. The rotational atherectomy system 10 may include a rotational atherectomy device 12 and a controller 14 for controlling the rotational atherectomy device 12. The rotational atherectomy device 12 may include a housing 16 and an elongate shaft 18 extending distally from the housing 16 to a cutting member 20 located at a distal end of the elongate shaft 18. The elongate shaft 18 may include a drive shaft 24 to provide rotational motion to the cutting member 20. In some instances, the elongate shaft 18 may include an outer tubular member 22 having a lumen extending therethrough and the drive shaft 24 may extend through the lumen of the outer tubular member 22. The drive shaft 24, which may be fixed to the cutting member 20, may be rotatable relative to the outer tubular member 22 to rotate the cutting member 20. In some instances the axial position of the cutting member 20 relative to the outer tubular member 22 may be adjusted by moving the drive shaft 24 longitudinally relative to the outer tubular member 22. For example, the atherectomy device 12 may include an advancer assembly 26 positioned in the housing 16, or otherwise provided with the housing 16, that is longitudinally movable relative to the housing 16. The outer tubular member 22 may be coupled to the housing 16 while the drive shaft 24 may be coupled to the advancer assembly 26. Accordingly, the drive shaft 24 (and thus the cutting member 20) may be longitudinally movable relative to the outer tubular member 22 by actuating the advancer assembly 26 relative to the housing 16.

The rotational atherectomy device 12 may include a prime mover 15 to provide rotational motion to the drive shaft 24 to rotate the cutting member 20. For example, in some instances the prime mover 15 may be a fluid turbine within the housing 16, such as provided with the advancer assembly 26. In other instances, however, the prime mover 15 may be an electrical motor, or the like. The controller 14 may be used to control the prime mover 15. For example, the user may provide power to the prime mover 15 and/or control the speed of rotation of the drive shaft 24 via the controller 14. For example, the front panel 28 of the controller 14 may include a user interface including a power switch, speed control mechanism (e.g., a speed control knob and/or buttons), a display, and/or other features for controlling the rotational atherectomy device 12. In some instances, the rotational atherectomy system 10 may include a remote control device 30, such as a foot pedal, a hand control, or other mechanism which may be used to control the power and/or speed to the prime mover 15, for example.

In instances in which the prime mover 15 is a turbine, the rotational atherectomy system 10 may also include a pressurized fluid source 32 providing a pressurized fluid to the turbine to rotate the drive shaft 24. In some instances, as shown, the pressurized fluid source 32 may be a tank of pressurized fluid (e.g., compressed air), which may or may not include an air compressor. In other instances, the pressured fluid source 32 may be provided external of the rotational atherectomy system 10, such as from a wall outlet at the medical facility. The pressured fluid source 32 may be coupled to the controller 14 via a fluid conduit 34, which in turn is coupled to the rotational atherectomy device 12 via a fluid conduit 36. The controller 14 may regulate the flow and/or pressure of fluid through the fluid conduit 36 to the rotational atherectomy device 12 to control the speed of rotation of the drive shaft 24 and cutting member 20, for instance.

In instances in which the prime mover 15 is an electric motor, the electric motor may be coupled to the controller 14 via an electrical connection to control the electric motor and/or provide electricity to the electric motor.

In some instances, the rotational atherectomy device 12 may include a speed sensor, such as an optical speed sensor, coupled to the controller 14 via a connector 38, such as a fiber optic connector to provide speed data to the controller 14. The speed data may be displayed on the front panel 28 and/or used to control the speed of the cutting member 20, such as maintaining a desired speed of the cutting member 20 during a medical procedure.

In some embodiments, the rotational atherectomy system 10 may be configured to infuse fluid through the elongate shaft 18 to the treatment site and/or aspirate fluid through the elongate shaft 18 from the treatment site. For example, the rotational atherectomy system 10 may include a fluid supply 40 for providing a flow of fluid through a lumen of the elongate shaft 18 to a treatment site. As shown in FIG. 1, in some instances the fluid supply 40 may include a saline bag 42 which may be pressurized by a pressure cuff 44 to provide a pressurized fluid (e.g., saline) to the rotational atherectomy device 12 through a fluid supply line 46. In other embodiments, an infusion pump, such as a peristaltic pump, may be used to deliver pressurized fluid to the rotational atherectomy device 12. Additionally or alternatively, in some embodiments the rotational atherectomy system 10 may be configured to aspirate fluid from the treatment site. For example, the rotational atherectomy system 10 may include an aspiration pump, such as a peristaltic pump, to generate a vacuum to aspirate fluid through a lumen of the elongate shaft 18 to a fluid collection container (not shown), if desired.

In some instances, the elongate shaft 18 of the rotational atherectomy device 12 may be advanced over a guidewire 48 to a treatment site. For example, the drive shaft 24 may include a guidewire lumen through which the guidewire 48 may pass. Additionally or alternatively, the elongate shaft 18 may be advanced through a lumen of a guide catheter to a treatment site.

Figure 2:
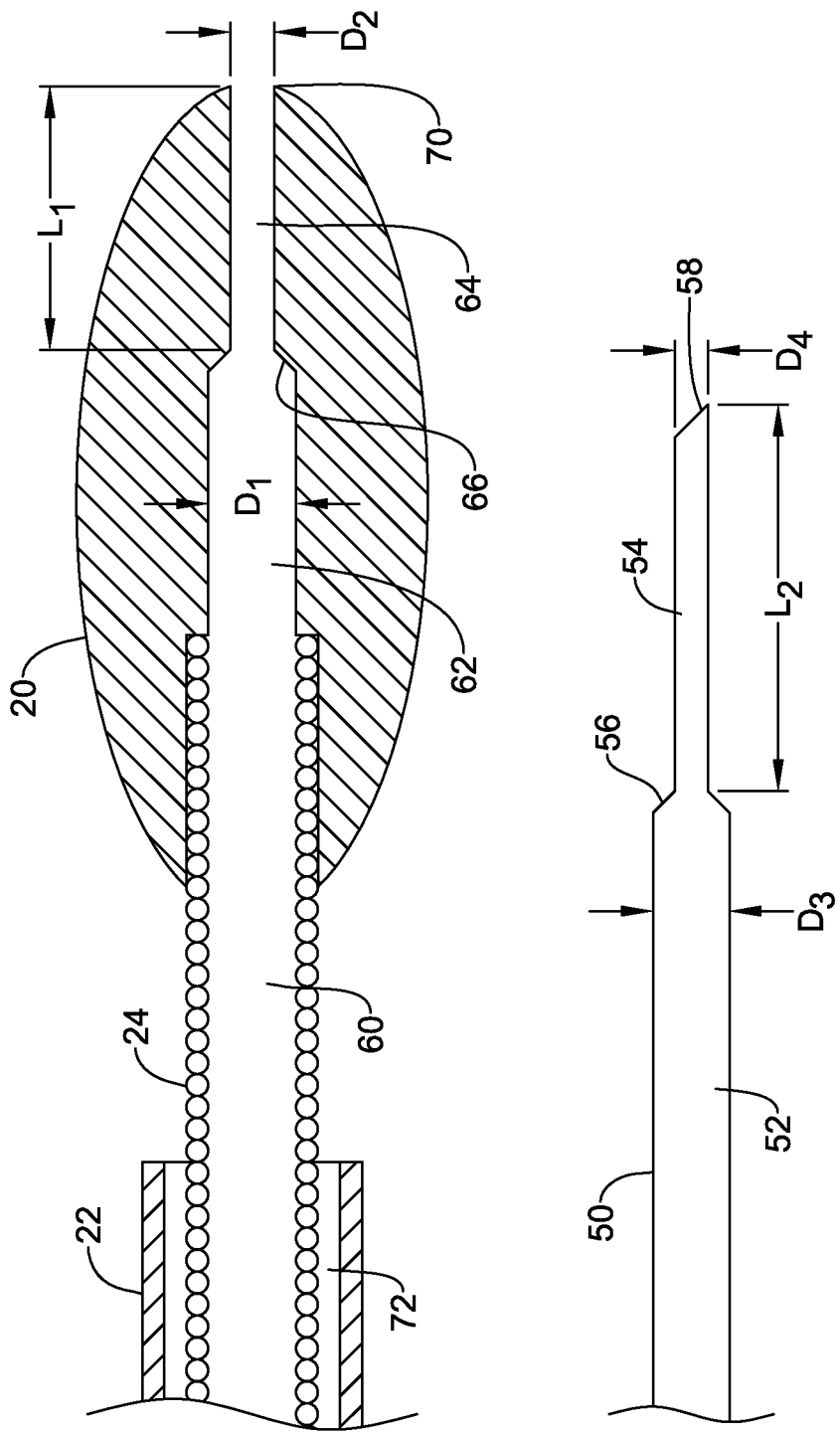
FIG. 2 is a cross-sectional view of a distal portion of components of an exemplary atherectomy system in accordance with the disclosure.

The distal region of components of the rotational atherectomy device 12 are shown in FIG. 2. As shown, the drive shaft 24, which in some instances may include a coiled member, may extend through the lumen 72 of the outer tubular member 22 and be rotationally and/or longitudinally movable relative to the outer tubular member 22. The drive shaft 24 may include the cutting member 20 mounted thereon. In some instances, the cutting member 20 may be a burr having an abrasive surface, such as a diamond coated abrasive surface. In other instances, the cutting member 20 may include one or more flutes having a cutting edge, or the cutting member 20 may be of another construction for abrading or cutting occlusive material.

A guidewire lumen 60 may extend through the drive shaft 24 and the cutting member 20 to a distal tip 70 of the cutting member 20. The guidewire lumen 60 may include a proximal portion 62 having a first diameter $D_1$ and a distal portion 64 having a second diameter $D_2$ less than the first diameter $D_1$ of the proximal portion 62 of the guidewire lumen 60. The guidewire lumen 60 may include an engagement feature 66, such as a stop, at a transition between the proximal portion 62 and the distal portion 64 of the guidewire lumen 60. For example, in some instances the engagement feature 66 may be a tapered or stepped surface forming a transition in diameter from the diameter of the proximal portion 62 to the distal portion 64 of the guidewire lumen 60. In other instances, the engagement feature 66 may be a protuberance, ring, key, or other element partially obstructing the guidewire lumen 60, for example. In other instances, the engagement feature 66 may be a change in shape of the guidewire lumen 60, forming a non-uniform interior surface of the guidewire lumen 60. The engagement feature 66 may be located at any longitudinal location of the guidewire lumen 60. In some instances, the engagement feature 66, such as a transition in diameter of the guidewire lumen 60, may be located proximate the cutting member 20. For example, as shown in FIG. 2, the engagement feature 66 may be located in a portion of the guidewire lumen 60 extending through the cutting member 20, or the engagement feature 66 may be located at a location along the drive shaft 24. In some instances, the engagement feature 66 may be located at the proximal end of the guidewire lumen 60.

An exemplary elongate penetrator 50 of the rotational atherectomy device 12 is also shown in FIG. 2. In some instances, the elongate penetrator 50 may be a guidewire positionable through the guidewire lumen 60 extending through the drive shaft 24 and the cutting member 20. The elongate penetrator 50 may be sized and configured to extend through the guidewire lumen 60 distal of the cutting member 20 a predetermined maximum distance. For example, the maximum distance the elongate penetrator 50 may extend from the distal tip 70 of the cutting member 20 may be controlled, at least in part, by the engagement of the engagement feature 66 of the guidewire lumen 60 with an engagement feature 56 of the elongate penetrator 50.

Figure 3:
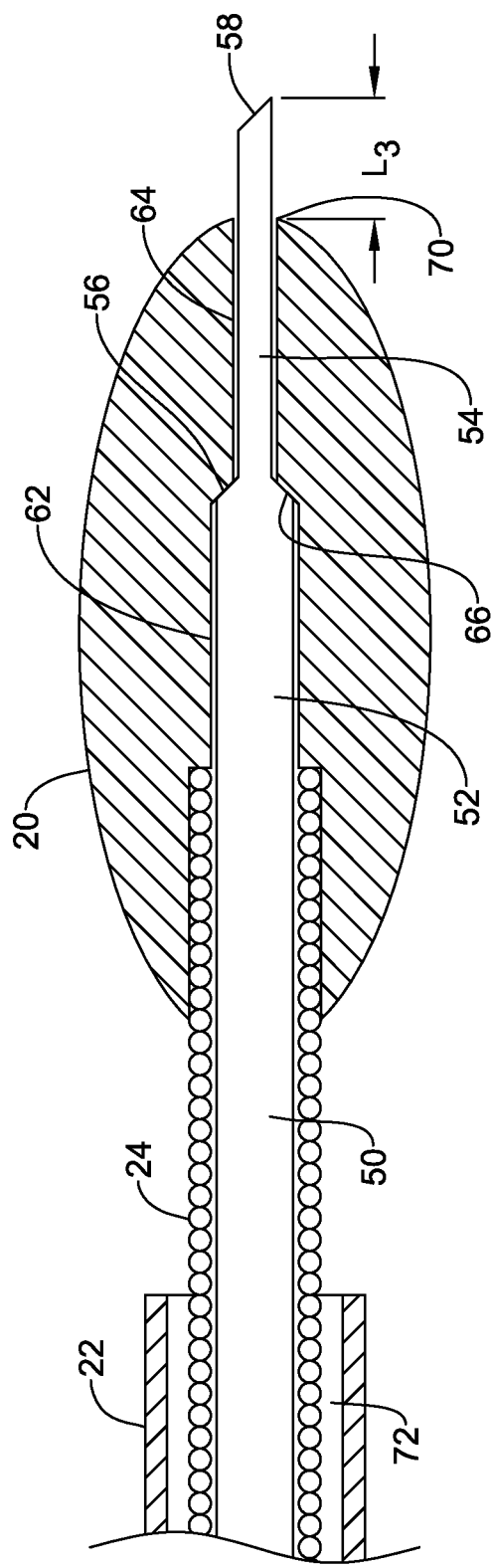
FIG. 3 is a cross-sectional view of the distal portion of the components of the exemplary atherectomy system of FIG. 2 assembled together.

In the illustrative embodiment, the elongate penetrator 50 may include a proximal portion 52 having a first diameter $D_3$ and a distal portion 54 having a second diameter $D_4$ less than the first diameter $D_3$ of the proximal portion 52 of the elongate penetrator 50. In some instances, the engagement feature 56, which may be a stop, may be positioned between and/or form a transition between the proximal portion 52 and the distal portion 54 of the elongate penetrator 50. For example, in some instances the engagement feature 56 may be a tapered or stepped surface forming a transition in diameter from the diameter of the proximal portion 52 to the distal portion 54 of the elongate penetrator 50. In other instances, the engagement feature 56 may be a protuberance, ring, key, or other element extending outward from the outer surface of the elongate penetrator 50, for example. In other instances, the engagement feature 56 may be a change in shape of the elongate penetrator 50, forming a non-uniform outer surface of the elongate penetrator 50. The engagement feature 56 may be located at any longitudinal location along the elongate penetrator 50. For example, as shown in FIG. 3, the engagement feature 56 may be located near the distal end of the elongate penetrator 50. In some instances, the engagement feature 56 may be located proximate a proximal end of the elongate penetrator 50 to engage with an engagement feature 66 at or near the proximal end of the guidewire lumen 60.

In the embodiment shown in FIG. 2, the distal portion 54 of the elongate penetrator 50 may extend from the engagement feature 56 to a distal tip 58 of the elongate penetrator 50, which in some instances may be a sharpened distal tip or otherwise configured to penetrate an occlusion.

The second diameter $D_4$ of the elongate penetrator 50 may be less than the second diameter $D_2$ of the guidewire lumen 60, while the first diameter $D_3$ of the elongate penetrator 50 may be greater than the second diameter $D_2$ of the guidewire lumen 60 such that only the distal portion 54 of the elongate penetrator 50 is positionable through the distal portion 64 of the guidewire lumen 60.

In some embodiments, the rotational atherectomy device 12 may be advanced to an occlusion in a blood vessel over a guidewire sized to pass through the distal portion 64 and the proximal portion 62 of the guidewire lumen 60. Subsequently, the guidewire may be withdrawn and the elongate penetrator 50 may be advanced distally through the guidewire lumen 60. In other instances, the rotational atherectomy device 12, which may include the elongate penetrator 50 positioned therein, may be advanced through a guide catheter to a treatment site, for example.

The engagement feature 66 of the guidewire lumen 60 and the engagement feature 56 of the elongate penetrator 50 may be arranged to permit the distal tip 58 of the elongate penetrator 50 to only extend distally from the distal tip 70 of the cutting member 20 a predetermined maximum distance when the elongate penetrator 50 is advanced distally through the guidewire lumen 60. For instance, the maximum distance may be predetermined by a mechanical stop or other engagement between the elongate penetrator 50 and the guidewire lumen 60 which prevents the elongate penetrator 50 from advancing further distally relative to the distal tip 70 of the cutting member 20. For example, the distal tip 70 of the cutting member 20 may be located a distance $L_1$ distal of the engagement feature 66 of the guidewire lumen 60 and the distal tip 58 of the elongate penetrator 50 may be located a distance $L_2$ distal of the engagement feature 56. The distance $L_2$ may be greater than the distance $L_1$, such that the distal tip 58 of the elongate penetrator 50 is positioned distal of the distal tip 70 of the cutting member 20 when the engagement feature 56 is engaged with the engagement feature 66 of the guidewire lumen 60, as shown in FIG. 3, when the elongate penetrator 50 is advanced distally through the guidewire lumen 60 a predetermined maximum distance $L_3$. In some instances, the predetermined maximum distance $L_3$ may be in the range of 0.2 millimeters to about 5 millimeters, about 0.5 millimeters to about 3 millimeters, about 0.5 to about 2 millimeters, about 0.5 millimeters to about 1.0 millimeter, about 1.0 millimeter to about 3.0 millimeters, about 1.0 millimeter to about 2.0 millimeters, or about 0.5 millimeters, about 1.0 millimeter, about 1.5 millimeters, about 2.0 millimeters, about 2.5 millimeters or about 3.0 millimeters, for example.

As discussed further herein, the distal tip 58 of the elongate penetrator 50, extending distally from the distal tip 70 of the cutting member 20 of the rotational atherectomy device 12, may be used to penetrate into the occlusion in a blood vessel prior to initiating engagement of the rotating cutting member 20 with the occlusion. Rotation of the cutting member 20, which may be rotatable independent of the elongate penetrator 50, may be initiated once the elongate penetrator 50 has been penetrated into the occlusion. Thus, the elongate penetrator 50 may stabilize the cutting member 20 as the cutting member 20 engages the occlusion to control the trajectory and advancement of the cutting member 20 through the occlusion.

Figure 4:
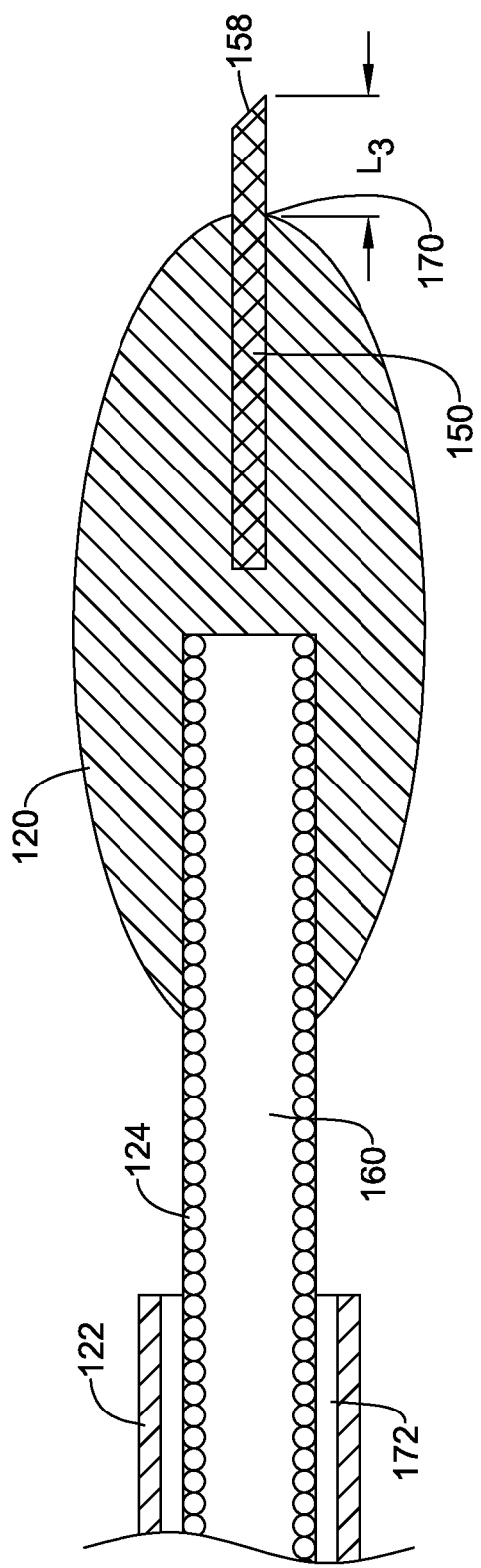
FIG. 4 is a cross-sectional view of a distal portion of another exemplary atherectomy system in accordance with the disclosure.

Another embodiment of the distal region of the rotational atherectomy device 12 is shown in FIG. 4. As shown, the drive shaft 124, which in some instances may include a coiled member, may extend through the lumen 172 of the outer tubular member 122 of the elongate shaft and be rotationally and/or longitudinally movable relative to the outer tubular member 122. The drive shaft 124 may include the cutting member 120 mounted thereon. In some instances, the cutting member 120 may be a burr having an abrasive surface, such as a diamond coated abrasive surface. In other instances, the cutting member 120 may include one or more flutes having a cutting edge, or the cutting member 120 may be of another construction for abrading or cutting occlusive material. In some instances, the drive shaft 124 may be hollow, including a lumen 160 extending therethrough to the cutting member 120.

An exemplary elongate penetrator 150 of the rotational atherectomy device 12 is also shown in FIG. 4. The elongate penetrator 150 may include a proximal end fixedly secured to the cutting member 120 and a distal tip 158 positioned distal of the distal tip 170 of the cutting member 120. The distal tip 158 may in some instances be a sharpened distal tip or otherwise configured to penetrate an occlusion. The elongate penetrator 150 may be fixedly secured to the cutting member 120 and/or the drive shaft 124 in any desired fashion such that the elongate penetrator 150 is rotatable with the cutting member 120 and drive shaft 124. For example, the elongate penetrator 150 may be welded, adhesively bonded, swaged, crimped, press-fit, or otherwise secured to the cutting member 120 and/or the drive shaft 124. The elongate penetrator 150 may be coaxial with the drive shaft 124, in some instances, such that the elongate penetrator 150 and the drive shaft 124 are rotatable about the same axis of rotation.

In some instances, the elongate penetrator 150 may be fixedly secured to the cutting member 120 such that the elongate penetrator 150 extends distal of the distal tip 170 of the cutting member 120 a predetermined maximum distance $L_3$. For instance, the maximum distance may be predetermined by fixing the position of the elongate penetrator 150 relative to the cutting member 120 with a portion of the elongate penetrator 150 extending distally of the cutting member 120. In some instances, the predetermined maximum distance $L_3$ may be in the range of 0.2 millimeters to about 5 millimeters, about 0.5 millimeters to about 3 millimeters, about 0.5 to about 2 millimeters, about 0.5 millimeters to about 1.0 millimeter, about 1.0 millimeter to about 3.0 millimeters, about 1.0 millimeter to about 2.0 millimeters, or about 0.5 millimeters, about 1.0 millimeters, about 1.5 millimeters, about 2.0 millimeters, about 2.5 millimeters or about 3.0 millimeters, for example.

As discussed further herein, the distal tip 158 of the elongate penetrator 150, extending distally from the distal tip 170 of the cutting member 120 of the rotational atherectomy device 12, may be used to penetrate into the occlusion in a blood vessel prior to initiating engagement of the rotating cutting member 120 with the occlusion. Rotation of the cutting member 120 may be initiated once the elongate penetrator 150 has been penetrated into the occlusion. Thus, the elongate penetrator 150 may stabilize the cutting member 120 as the cutting member 120 engages the occlusion to control the trajectory and advancement of the cutting member 120 through the occlusion.

Figure 5:
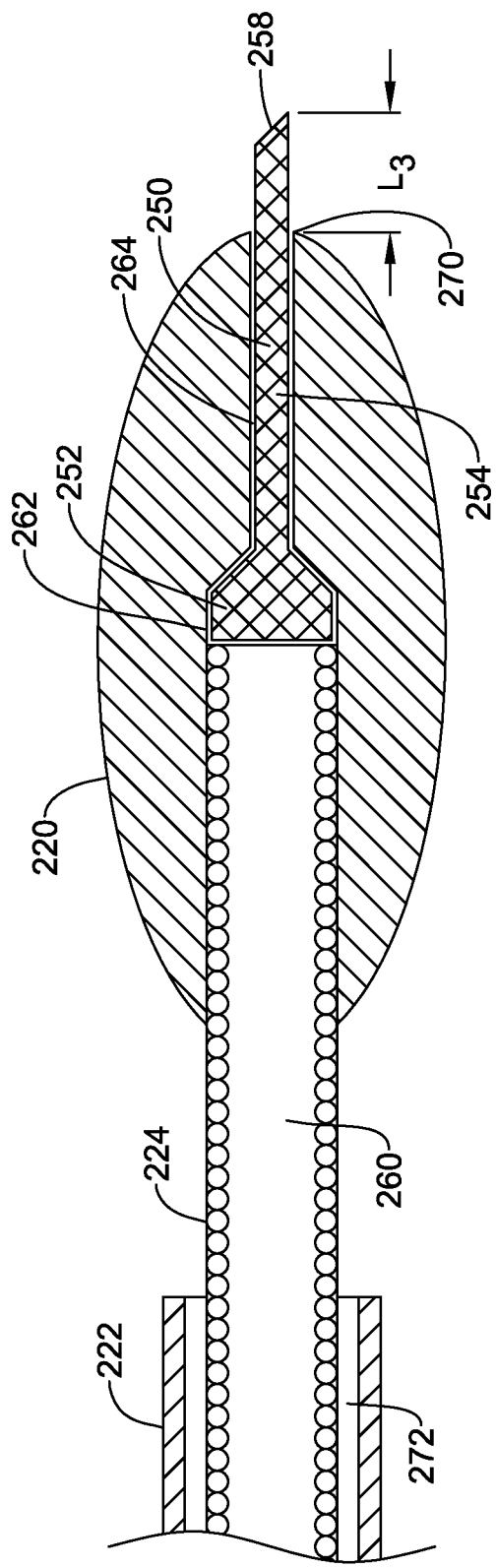
FIG. 5 is a cross-sectional view of a distal portion of another exemplary atherectomy system in accordance with the disclosure.

Another embodiment of the distal region of the rotational atherectomy device 12 is shown in FIG. 5. As shown, the drive shaft 224, which in some instances may include a coiled member, may extend through the lumen 272 of the outer tubular member 222 of the elongate shaft and be rotationally and/or longitudinally movable relative to the outer tubular member 222. The drive shaft 224 may include the cutting member 220 mounted thereon. In some instances, the cutting member 220 may be a burr having an abrasive surface, such as a diamond coated abrasive surface. In other instances, the cutting member 220 may include one or more flutes having a cutting edge, or the cutting member 220 may be of another construction for abrading or cutting occlusive material. In some instances, the drive shaft 224 may be hollow, including a lumen 260 extending therethrough to the cutting member 220.

An exemplary elongate penetrator 250 of the rotational atherectomy device 12 is also shown in FIG. 5. The elongate penetrator 250, which may be coaxial with the drive shaft 224 in some instances, may include a proximal end rotatably coupled to the cutting member 220 and a distal tip 258 positioned distal of the distal tip 270 of the cutting member 220. The distal tip 258 may in some instances be a sharpened distal tip or otherwise configured to penetrate an occlusion. The elongate penetrator 250 may be rotatably coupled to the cutting member 220 and/or the drive shaft 224 in any desired fashion such that the cutting member 220 and drive shaft 224 are rotatable independent of elongate penetrator 250.

In the illustrated embodiment, the elongate penetrator 250 may include a proximal enlarged portion 252 having a first cross-sectional dimension (e.g., diameter) and a distal portion 254 having a second cross-sectional dimension (e.g., diameter) less than the first cross-sectional dimension of the proximal portion 252 of the elongate penetrator 250. The distal portion 254 may extend distal of the distal tip 270 of the cutting member 220 to the distal tip 258 of the elongate penetrator 250. The cutting member 220 may include a lumen including a proximal enlarged portion 262 having a first cross-sectional dimension (e.g., diameter) and a distal portion 264 having a second cross-sectional dimension (e.g., diameter) less than the first cross-sectional dimension of the proximal portion 262. The cross-sectional dimension of the enlarged portion 252 of the elongate penetrator 250 may be greater than the cross-sectional dimension of the distal portion 264 of the lumen, while the cross-sectional dimension of the distal portion 254 of the elongate penetrator 250 may be less than the cross-sectional dimension of the distal portion 264 of the lumen, such that the enlarged portion 252 is unable to pass through the distal portion 264 of the lumen.

The enlarged portion 252 of the elongate penetrator 250 may be rotatably retained in the enlarged proximal portion of the lumen by any desired means. For example, a distal end portion of the drive shaft 224 may be inserted into the enlarged portion 262 of the lumen and secured therein, capturing the enlarged portion 252 of the elongate penetrator 250 between the distal end of the drive shaft 224 and the distal portion 264 of the lumen of the cutting member 220. The drive shaft 224 may be sized to prevent the enlarged portion 252 from moving proximally in the lumen.

In some instances, the elongate penetrator 250 may extend distal of the distal tip 270 of the cutting member 220 a predetermined maximum distance $L_3$. For instance, the maximum distance may be predetermined by a mechanical stop or other engagement between the elongate penetrator 250 and the cutting member 220 which prevents the elongate penetrator 250 from displacement distally relative to the distal tip 270 of the cutting member 220. In some instances, the predetermined maximum distance $L_3$ may be in the range of 0.2 millimeters to about 5 millimeters, about 0.5 millimeters to about 3 millimeters, about 0.5 to about 2 millimeters, about 0.5 millimeters to about 1.0 millimeter, about 1.0 millimeter to about 3.0 millimeters, about 1.0 millimeter to about 2.0 millimeters, or about 0.5 millimeters, about 1.0 millimeters, about 1.5 millimeters, about 2.0 millimeters, about 2.5 millimeters or about 3.0 millimeters, for example.

As discussed further herein, the distal tip 258 of the elongate penetrator 250, extending distally from the distal tip 270 of the cutting member 220 of the rotational atherectomy device 12, may be used to penetrate into the occlusion in a blood vessel prior to initiating engagement of the rotating cutting member 220 with the occlusion. Rotation of the cutting member 220, which may be rotatable independent of the elongate penetrator 250, may be initiated once the elongate penetrator 250 has been penetrated into the occlusion. Thus, the elongate penetrator 250 may stabilize the cutting member 220 as the cutting member 220 engages the occlusion to control the trajectory and advancement of the cutting member 220 through the occlusion.

Figure 6:
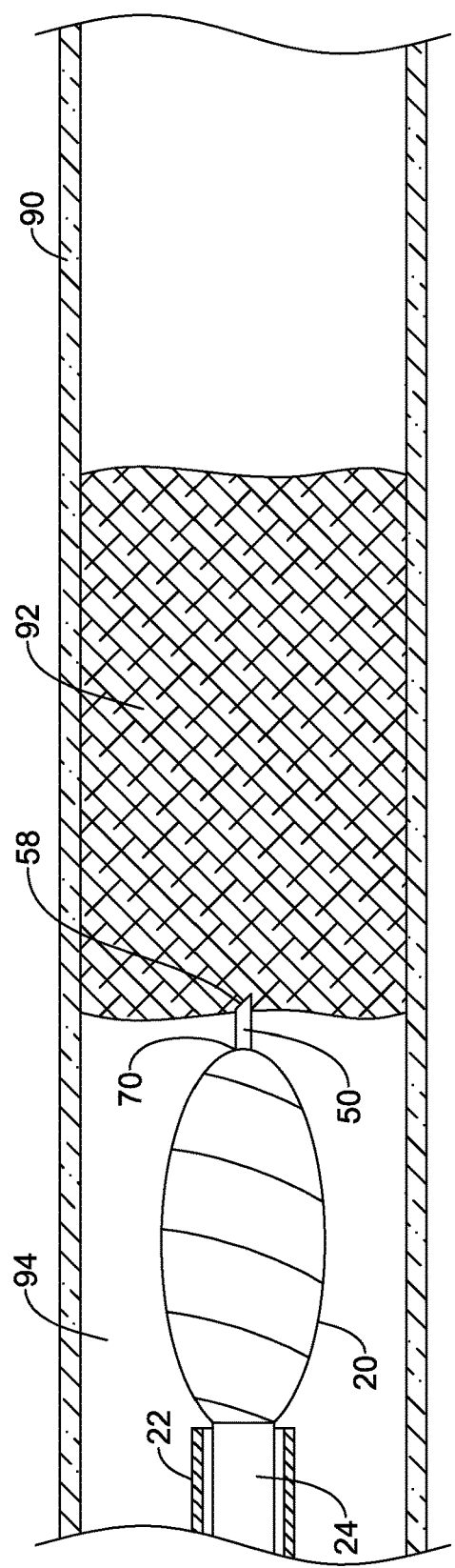
FIGS. 6-8 illustrate aspects of an exemplary method of traversing an occlusion in a blood vessel.
Figure 7:
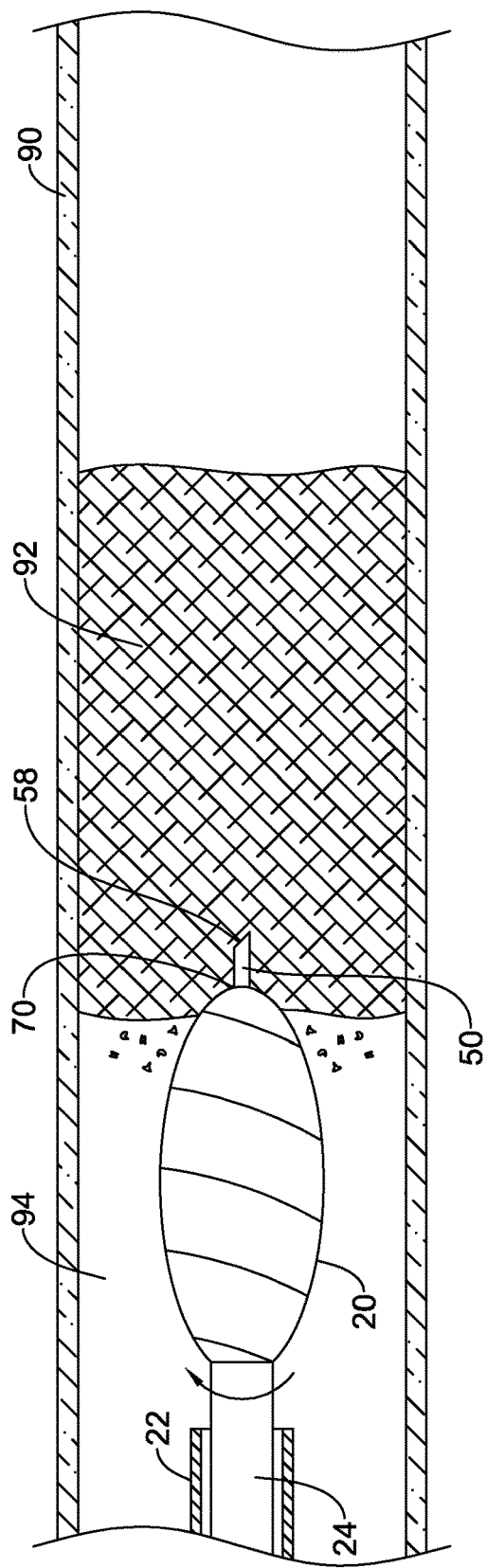
Figure 8:
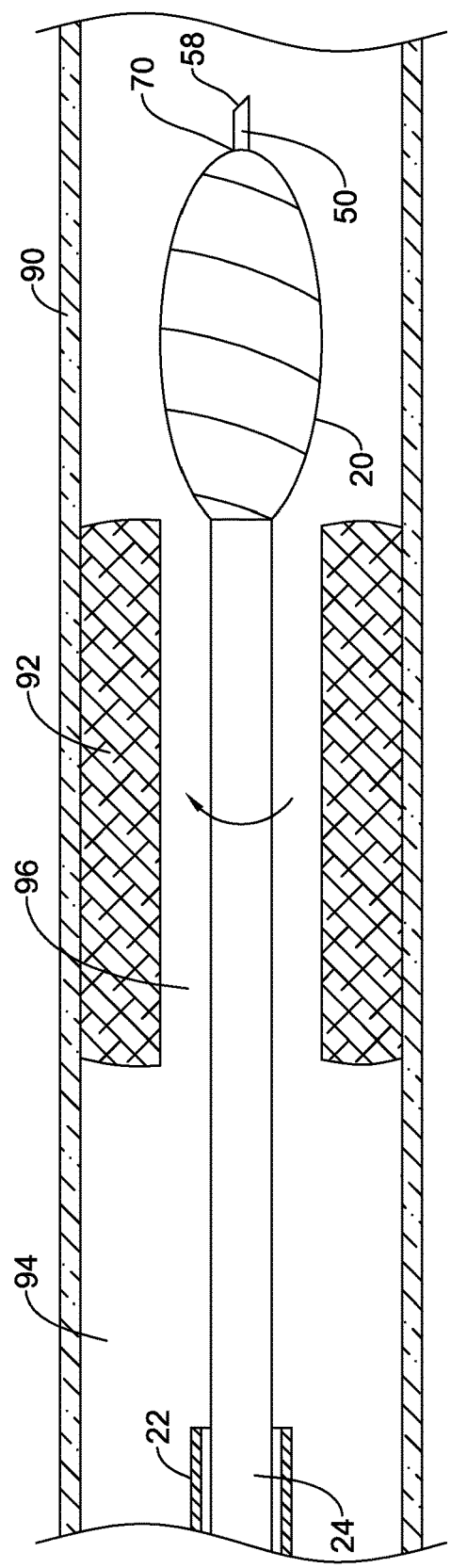

Turning now to FIGS. 6-8, aspects of an exemplary method of traversing an occlusion in a blood vessel are shown. As shown, the rotational atherectomy device 12 may be advanced through the lumen 94 of the blood vessel 90 to an occlusion 92 to create or enlarge a passageway through the occlusion 92. For instance, the elongate shaft 18 of the rotational atherectomy device 12 may be advanced through a body lumen (e.g., blood vessel 90) to a location proximal of the occlusion 92 in the body lumen. In some instances, the elongate shaft 18 of the rotational atherectomy device 12 may be advanced through the lumen 94 over a guidewire to the occlusion 92. For example, the drive shaft 24 may include a guidewire lumen through which the guidewire may pass through. Additionally or alternatively, the elongate shaft 18 may be advanced through a lumen of a guide catheter to the occlusion 92. The rotational atherectomy device 12 may be advanced to the location proximal of the occlusion 92 without previously positioning a guidewire across the occlusion 92 in instances in which it may be difficult or impossible to position a guidewire across the occlusion 92 prior to advancing the rotational atherectomy device 12 to the occlusion 92.

In instances in which the rotational atherectomy device 12 is advanced over a guidewire to the occlusion 92, the guidewire may then be withdrawn from the guidewire lumen of the elongate shaft 18, and then the elongate penetrator 50 may be advanced through the guidewire lumen until the distal tip 58 of the elongate penetrator 50 is positioned distal of the distal tip 70 of the cutting member 20, such as positioned at the predetermined maximum distance distal of the distal tip 70 of the cutting member 20. As discussed above, the elongate penetrator 50 may include an engagement feature configured to engage an engagement feature of the guidewire lumen when the elongate penetrator 50 is extended to the predetermined maximum distance, preventing further distal advancement of the distal tip 58 of the elongate penetrator 50 beyond the predetermined maximum distance from the cutting member 20.

In other instances, the cutting member 20 of the rotational atherectomy device 12 may be advanced to the occlusion 92 with the elongate penetrator 50 extending distally from the distal tip 70 of the cutting member 20, such as when the elongate penetrator (e.g., the elongate penetrator 150, 250) is coupled to and advanced with the cutting member 20.

Once positioned proximate the occlusion 92, the distal tip 58 of the elongate penetrator 50 may be advanced distally to penetrate into the occlusion 92, as shown in FIG. 6. Since the distal tip 58 is located distally of the cutting member 20, the elongate penetrator 50 may penetrate into the occlusion 92 prior to the cutting member 20 contacting the occlusion 92.

Turning to FIG. 7, thereafter, rotation of the cutting member 20 may be initiated once the elongate penetrator 50 has been penetrated into the occlusion 92 and advanced into the occlusion 92. Thus, the elongate penetrator 50 may stabilize the cutting member 20 as the cutting member 20 engages the occlusion 92 to control the trajectory and advancement of the cutting member 20 through the occlusion 92. The rotatable drive shaft 24 extending through the outer tubular member 22 of the elongate shaft 18 of the rotational atherectomy device 12 may be rotatably driven to rotatably drive the cutting member 20 while advancing the cutting member 20 through the occlusion 92. In some instances, the cutting member 20 may rotate while the elongate penetrator 50 remains stationary, while in other instances the elongate penetrator 50 may rotate with the cutting member 20. In some instances the drive shaft 24 may be advanced distally relative to the outer tubular member 22 to advance the cutting member 20 through the occlusion 92, while in other instances the outer tubular member 22 may be advanced together with the drive shaft 24. In some instances, fluid infusion and/or fluid aspiration through one or more lumens of the rotational atherectomy device 12 may be performed while advancing the cutting member 20 through the occlusion 92.

The cutting member 20 may be advanced through the occlusion 92 to form or enlarge a pathway 96 through the occlusion 92 to permit blood flow through the lumen 94 of the blood vessel 90, as shown in FIG. 8. In some instances, the distal tip 58 of the elongate penetrator 50 may be maintained distal of the distal tip 70 of the cutting member 20 throughout advancement of the cutting member 20 entirely through the occlusion 92. In other instances, once the cutting member 20 has been partially advanced into the occlusion 92, the distal tip 58 of the elongate penetrator 50 may be withdrawn proximal of the distal tip 70 of the cutting member 20 such that the distal tip 70 is the distal most portion during further advancement of the cutting member 20 through the occlusion 92.

It is noted that the rotational cutting devices described herein may be used in other medical procedures, such as in orthopedic medical procedures, if desired. For example, the penetrating member may be penetrated into a bony structure to stabilize the cutting member prior to initiating engagement of the rotating cutting member with the bony structure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A rotational atherectomy device, comprising:
   an outer tubular member having a lumen extending therethrough;
   a cutting member rotationally positioned at a distal end of the outer tubular member;
   a drive shaft, having an outer diameter less than an outer diameter of the cutting member, extending through the lumen of the outer tubular member, the drive shaft rotatable relative to the outer tubular member to rotate the cutting member;
   a prime mover attached to a proximal end of the drive shaft to provide rotational motion to the drive shaft; and
   an elongate penetrator extendable distal of the cutting member a maximum distance, wherein the maximum distance is predetermined and is in the range of 0.2 millimeters to 5.0 millimeters.

2. The rotational atherectomy device of claim 1, wherein the elongate penetrator is positionable through a lumen extending through the drive shaft and the cutting member.

3. The rotational atherectomy device of claim 2, wherein the elongate penetrator includes an engagement feature configured to engage an engagement feature of the lumen of the drive shaft when extended to the maximum distance.

4. The rotational atherectomy device of claim 3, wherein the engagement feature of the elongate penetrator includes a transition in diameter and the engagement feature of the lumen of the drive shaft includes a transition in diameter.

5. The rotational atherectomy device of claim 4, wherein the transition in diameter of the lumen of the drive shaft is located proximate the cutting member.

6. The rotational atherectomy device of claim 2, wherein the elongate penetrator includes a proximal portion having a first diameter and a distal portion having a second diameter less than the first diameter of the proximal portion of the elongate penetrator;
   wherein the lumen of the drive shaft includes a proximal portion having a first diameter and a distal portion having a second diameter less than the first diameter of the proximal portion of the lumen of the drive shaft; and wherein the second diameter of the elongate penetrator is less than the second diameter of the lumen of the drive shaft and the first diameter of the elongate penetrator is greater than the second diameter of the lumen of the drive shaft, such that only the distal portion of the elongate penetrator is positionable through the distal portion of the lumen of the drive shaft.

7. The rotational atherectomy device of claim 1, wherein the elongate penetrator is rotatable with the cutting member.

8. The rotational atherectomy device of claim 1, wherein the cutting member is rotatable independent of the elongate penetrator.

9. The rotational atherectomy device of claim 1, wherein the elongate penetrator includes a sharpened distal tip.

10. A rotational atherectomy device, comprising:
an outer tubular member having a lumen extending therethrough;
a cutting member rotationally positioned at a distal end of the outer tubular member;
a drive shaft, having an outer diameter less than an outer diameter of the cutting member, extending through the lumen of the outer tubular member, the drive shaft rotatable relative to the outer tubular member to rotate the cutting member;
a prime mover attached to a proximal end of the drive shaft to provide rotational motion to the drive shaft;
a guidewire lumen extending through the drive shaft and the cutting member; and
an elongate guidewire extendable through the guidewire lumen from a proximal end to a distal end of the cutting member;
the guidewire including a distal tip and a stop configured to engage a stop in the guidewire lumen to prevent distal advancement of the distal tip of the guidewire beyond a predetermined maximum distance distally beyond the cutting member.

11. The rotational atherectomy device of claim 10, wherein the stop of the guidewire includes a transition in diameter and the stop of the guidewire lumen includes a transition in diameter.

12. The rotational atherectomy device of claim 11, wherein the transition in diameter of the guidewire is located between a proximal portion of the guidewire having a first diameter and a distal portion of the guidewire having a second diameter less than the first diameter of the proximal portion of the guidewire;
wherein the transition in diameter of the guidewire lumen is located between a proximal portion of the guidewire lumen having a first diameter and a distal portion of the guidewire lumen having a second diameter less than the first diameter of the proximal portion of the guidewire lumen; and wherein the second diameter of the guidewire is less than the second diameter of the guidewire lumen and the first diameter of the guidewire is greater than the second diameter of the guidewire lumen, such that only the distal portion of the guidewire is positionable through the distal portion of the guidewire lumen.

13. The rotational atherectomy device of claim 11, wherein the transition in diameter of the guidewire lumen is located proximate the cutting member.

14. The rotational atherectomy device of claim 10, wherein the predetermined maximum distance is in the range of 0.5 millimeters to 2.0 millimeters.

15. The rotational atherectomy device of claim 10, wherein the predetermined maximum distance is in the range of 0.2 millimeters to 5.0 millimeters.

16. A rotational atherectomy device, comprising:
an outer tubular member having a lumen extending therethrough;
a drive shaft extending through the lumen of the outer tubular member and rotatable relative to the outer tubular member;
a cutting member fixed to a distal end of the drive shaft and rotatable therewith;
a prime mover attached to a proximal end of the drive shaft to provide rotational motion to the drive shaft and the cutting member;
a guidewire lumen extending through the drive shaft and the cutting member, the guidewire lumen including an engagement surface at a transition between a proximal portion of the guidewire lumen and a distal portion of the guidewire lumen; and
an elongate penetrator positionable through the guidewire lumen from a proximal end to a distal end of the guidewire lumen, the elongate penetrator including an engagement surface configured to engage with the engagement surface of the guidewire lumen to prevent distal movement of the elongate penetrator beyond a distal end of the cutting member a predetermined maximum distance.

17. The rotational atherectomy device of claim 16, wherein the elongate penetrator includes a sharpened distal tip configured to engage an occlusion.

18. The rotational atherectomy device of claim 16, wherein the elongate penetrator includes a proximal region proximal of the engagement surface of the elongate penetrator and a distal region distal of the engagement surface of the elongate penetrator, wherein the proximal region has an outer diameter greater than an outer diameter of the distal region.

19. The rotational atherectomy device of claim 16, wherein the predetermined maximum distance is in the range of 0.2 millimeters to 5.0 millimeters.

20. The rotational atherectomy device of claim 16, wherein the engagement surface of the guidewire lumen is disposed within the cutting member.

* * * * *